(12) United States Patent  
Park et al.

(10) Patent No.: US 8,399,044 B2  
(45) Date of Patent: Mar. 19, 2013

(54) METHOD FOR COATING MEDICATION ON MEDICAL ARTICLE

(75) Inventors: Jong-Sang Park, Seoul (KR); Dae-Joong Kim, Seongnam-si (KR); In-Su Baek, Anyang-si (KR); Chengzhe Bai, Seoul (KR)

(73) Assignee: SNU R and DB Foundation, Seoul (KR)

( * ) Notice: Subject to any disclaimer, the term of this patent is extended or adjusted under 35 U.S.C. 154(b) by 364 days.

(21) Appl. No.: 12/809,054

(22) PCT Filed: Jan. 21, 2010

(86) PCT No.: PCT/KR2010/000393  
§ 371 (c)(1), (2), (4) Date: Jun. 17, 2010

(87) PCT Pub. No.: WO2011/090224  
PCT Pub. Date: Jul. 28, 2011

(65) Prior Publication Data  
US 2011/0183064 A1 Jul. 28, 2011

(51) Int. Cl.
| | |
|---|---|
| A61F 13/00 | (2006.01) |
| A61F 13/02 | (2006.01) |
| A61K 9/28 | (2006.01) |
| A61K 9/70 | (2006.01) |
| A61B 17/04 | (2006.01) |
| A61B 17/10 | (2006.01) |
| A61L 17/00 | (2006.01) |
| A61M 31/00 | (2006.01) |
| B01J 13/00 | (2006.01) |
| B05D 3/00 | (2006.01) |
| B32B 19/00 | (2006.01) |
| D02G 3/00 | (2006.01) |

(52) U.S. Cl. ...... 427/2.31; 427/2.21; 424/443; 424/474; 606/139; 606/228; 604/502; 428/357; 428/364

(58) Field of Classification Search ................ 427/2.21, 427/2.31; 424/443, 474; 606/139, 228; 604/502; 428/357, 364  
See application file for complete search history.

(56) References Cited

U.S. PATENT DOCUMENTS

| | | | | |
|---|---|---|---|---|
| 5,788,979 | A | * | 8/1998 | Alt et al. .................. 424/426 |
| 6,919,100 | B2 | * | 7/2005 | Narayanan ................ 427/2.24 |
| 7,090,888 | B2 | * | 8/2006 | Snyder et al. ............. 427/2.21 |
| 7,303,814 | B2 | * | 12/2007 | Lamberti et al. .......... 428/357 |
| 7,829,133 | B2 | * | 11/2010 | Vogt et al. ................. 427/2.31 |

FOREIGN PATENT DOCUMENTS

| | | | |
|---|---|---|---|
| KR | 10-0496354 | * | 6/2005 |
| KR | 10-2008-0078113 | * | 8/2008 |
| KR | 10-2011-0085700 | * | 7/2011 |

OTHER PUBLICATIONS

"Pulsatile drug release control using hydrogels," Akihiko Kikuchi et al. Advanced Drug Delivery Reviews 54 (2002), pp. 53-77.*

* cited by examiner

*Primary Examiner* — Patricia L Hailey  
(74) *Attorney, Agent, or Firm* — Intellectual Property Law Group LLP

(57) ABSTRACT

A method for coating medication for a medical product is disclosed. A technique for coating gel in a viscous semisolid state is provided to facilitate coating of medication. Coating of medication on an article can be facilitated using gel, and coating of medication on an article such as an article made of silk and an article made of polypropylene can be further facilitated.

12 Claims, 6 Drawing Sheets

METHOD FOR COATING MEDICATION ON MEDICAL ARTICLE

CROSS-REFERENCE TO RELATED APPLICATION

This application is a U.S. National Phase application, under 35 U.S.C. §371, of International Application no. PCT/KR2010/000393, with an international filing date of Jan. 21, 2010, which is hereby incorporated by reference for all purposes.

BACKGROUND OF THE INVENTION

1. Field of the Invention

The present invention relates to a method for coating medication (e.g., a medicinal substance, a medicinal liquid, medicine, etc.) on a medical article.

2. Background of the Invention

In general, a suture, thread used for medical purposes, is a medical product (e.g., a medical article) used for bonding the tissue of a person (e.g., a patient) while the tissue is healing after an operation. A portion of the tissue of a person, such as the skin or a blood vessel, is sutured. The suture pulls the skin tightly together to attach the part which has been opened due to an operation or an injury to promote rapid healing. In that case, however, when the tissue, in particular, the torn part of the skin, is stitched using a conventional suture, the growth of cells is interfered with at the stitched part, i.e., the part penetrated by the thread, thus leaving an unsightly scar.

In addition, although the suture is living body adaptive, its presence in the living body acts as a foreign body and causes inflammation in the ambient living body tissue. That is, an adverse reaction to the suture may be generated causing an inflammation such as the generation of pus at the portion of skin penetrated by the suture.

In particular, when blood vessels are sutured or when a blood vessel and an artificial blood vessel are sutured, thrombosis is generated at the part stitched by the suture, and blood flow is interfered with due to constriction of blood vessels caused by neointimal hyperplasia.

Therefore, as one of solutions to the problem, a technique for coating a material to assist the treatment of the suture has been proposed. However, coating such a material on the suture is not easy, controlling of eluting of the coated material is difficult, and the effect of the coated material is impermanent.

SUMMARY OF THE INVENTION

The present invention solves the above problems, and provides a method for coating medication on a medical article capable of facilitating the coating of medication.

In accordance with an exemplary embodiment of the present invention, there is provided a method for coating medication on a medial article, including: a medication coating step of coating medication on the surface of an article used for a medical purpose; and gel coating step of coating gel in a viscous semisolid state on the surface of the medication-coated article.

Preferably, the article is source thread. The gel is a mixture of gelatin, dextran, and glyceraldehyde. The gelatin, dextran, and glyceraldehyde are mixed in an aqueous solution state. The gel is a mixture of gelatin, dextran, and glutaraldehyde.

Preferably, the method may further include a gel surface coating step of coating a material for smoothing the surface of the gel on the surface of the article after the article is coated with the gel.

Preferably, the material for smoothing the surface of the gel is one or more of polycaprolactone (PCL), polyglycolic acid (PGA), polylactic acid (PLA), polylactic-co-glycolic acid (PLGA), and polyethylene glycol (PEG).

Preferably, after the gel is coated on the surface of the article, a material for smoothing the surface of the gel is further coated.

Preferably, the amount of the gel coated on the article is adjustable according to gelation of the gel.

Preferably, a speed at which the medication spurts out varies according to a gelation state of the gel.

Preferably, time during which the gel is coated and gelated on the article varies according to density and temperature of the gel.

In accordance with another exemplary embodiment of the present invention, there is provided a method for coating medication on a medical article, including: a gel coating step of coating gel in a viscous semisolid state on the surface of an article used for a medical purpose; and a medication coating step of coating medication on the surface of the gel-coated article.

Preferably, the coating medication is one of putting the gel-coated article in medication to coat the article or spraying the medication with a spray to coat the article.

Preferably, the gel is a mixture of gelatin, dextran, and glyceraldehyde. The gelatin, dextran, and glyceraldehyde are mixed in an aqueous solution state. The gel is a mixture of gelatin, dextran, and glutaraldehyde.

Preferably, the method may further include a gel surface coating step of coating a material for smoothing the surface of the gel on the surface of the article after the article is coated with the gel.

Preferably, the material for smoothing the surface of the gel is one or more of polycaprolactone (PCL), polyglycolic acid (PGA), polylactic acid (PLA), polylactic-co-glycolic acid (PLGA), and polyethylene glycol (PEG).

Preferably, after the gel is coated on the surface of the article, a material for smoothing the surface of the gel is further coated.

Preferably, the amount of the gel coated on the article is adjustable according to gelation of the gel.

Preferably, a speed at which the medication spurts out varies according to a gelation state of the gel.

Preferably, time during which the gel is coated and gelated on the article varies according to density and temperature of the gel.

In accordance with another exemplary embodiment of the present invention, there is provided a method for coating medication on a medical article, including: a mixing step of generating a mixture material obtained by mixing gel to be coated on the surface of an article used for a medical purpose and medication; and a mixture material coating step of coating the mixture material on the surface of the article.

Preferably, the medication mixed in the mixture material is a water-soluble medication.

Preferably, the article is source thread. The gel is a mixture of gelatin, dextran, and glyceraldehyde. The gelatin, dextran, and glyceraldehyde are mixed in an aqueous solution state. The gel is a mixture of gelatin, dextran, and glutaraldehyde.

Preferably, the method may further include a gel surface coating step of coating a material for smoothing the surface of the gel on the surface of the article after the article is coated with the gel.

Preferably, the material for smoothing the surface of the gel is one or more of polycaprolactone (PCL), polyglycolic acid (PGA), polylactic acid (PLA), polylactic-co-glycolic acid (PLGA), and polyethylene glycol (PEG).

Preferably, after the gel is coated on the surface of the article, a material for smoothing the surface of the gel is further coated.

Preferably, the amount of the gel coated on the article is adjustable according to gelation of the gel.

Preferably, a speed at which the medication spurts out varies according to a gelation state of the gel.

Preferably, time during which the gel is coated and gelated on the article varies according to density and temperature of the gel.

BRIEF DESCRIPTION OF THE DRAWINGS

The features and advantages of the present invention will become more apparent from the following detailed description in conjunction with the accompanying drawings, in which.

DETAILED DESCRIPTION OF THE INVENTION

Figure 1:
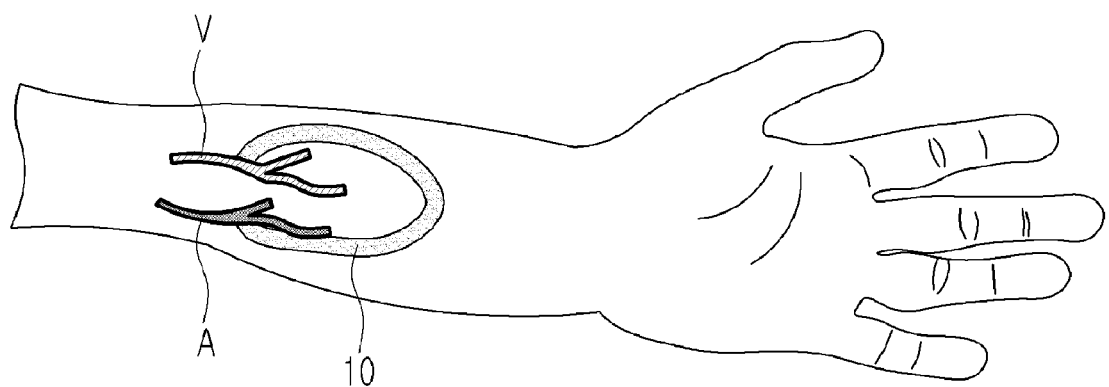
FIG. 1 illustrates an application of suture according to an exemplary embodiment of the present invention.

Hereinafter, exemplary embodiments of the present invention are described in detail with reference to the accompanying drawings. Detailed descriptions of well-known functions and structures incorporated herein may be omitted to avoid obscuring the subject matter of the present invention.

A method for coating medication for a medical article according to exemplary embodiments of the present invention will now be described with reference to FIGS. 1 to 7. In exemplary embodiments of the present invention, medical thread, one of medical articles (or medical products), will be taken as an example, and further, the present invention can be applied to an artificial blood vessel, etc.

First, medical thread (referred to as 'suture') according to an exemplary embodiment of the present invention may be used to stitch the skin in order to suture the part that is open due to an operation or an injury, or may be used to connect an artery A of a patient and a vein V for the purpose of anastomosing an artificial blood vessel.

In an exemplary embodiment of the present invention, a viscose semi-solid gel (g) 10 is used to coat medication M on a source thread T. In this case, to obtain the gel (g) 10, gelatin, dextran, and glyceraldehyde, etc., are mixed into an aqueous solution state, and as the aqueous solution is gelated to be hardened into the form of the gel (g) 10.

In this case, gelatin, which is a sort of induced protein obtained by processing collagen, natural protein, constituting the skin, tendon, cartilage, and the like, of animals with hot water, is used as a hemostatic agent and the like.

Dextran is a glucan containing complicated chains, each with various lengths, having branches. Dextran may be used as a raw material of syrup, or partially hydrolyzed with acid and melted by about 6 percent in a physiological salt solution so as to be used as a substitute serum.

Glyceraldehyde is a compound generated during a carbohydrate metabolism process, a colorless crystalline solid. Glyceraldehyde is glycerin formed as one hydroxide is changed into one aldehyde group, having properties that allow it to easily melt in water and alcohol and it appears as an intermediate material in a reaction within a living body.

Meanwhile, instead of glyceraldehyde, glutaraldehyde applicable to an exemplary embodiment of the present invention can be mixed to be used.

It is formed to facilitate the coating of medication M on the source thread T using the gel (g), and in this case, the gelation time varies according to the density of the components constituting the gel (g) and a reaction temperature, and it is configured such that the speed at which the medication spurts out varies according to the gelation state.

Also, the amount of the gel (g) coated on the source thread T can be adjusted based on the fact that the viscosity increases according to the gelation. For example, when a large amount of gel (g) is desired to be coated on the source thread T, gel (g) which has been considerably gelated to have a high viscosity may be used to coat the source thread T, and when a small amount of gel (g) is desired to be coated, gel (g) which has been just started to be gelated to have a low viscosity may be used to coat the suture 10.

In that case, the process of generating gel (g) to be applied for the exemplary embodiment of the present invention is performed in a state of an aqueous state, facilitating the coating of the aqueous medication M, and preferably, the suture 10 used for suturing the skin is coated with a material capable of restraining the generation of inflammation on the surface of the skin and medication M capable of quickly healing the stitched part without a scar.

If the coated medication M is mixed with gel (g) so as to be coated as a mixture material G, an aqueous medication may be preferably used, and when the medication M and the gel (g) are coated in different stages, a fat-soluble medication, as well as an aqueous medication, may be also used for coating.

For example, basic Fibroblast Growth Factor (bFGF) may be used as a material for quickly healing up the stitched part without a scar, and such material may be classified as a growth factor.

Meanwhile, gel (g) may be unsuitable to be used for the purpose of anastomosing an artificial blood vessel, so in such a case, Polycaprolactone (PCL), Polyglycolic acid (PGA), Polylactic acid (PLA), Polylactic-co-glycolic acid (PLGA), Polyethylene glycol (PEG), etc. may be also used to be coated together to smooth the surface of the gel (g).

Here, PCL, PGA, PLA, PLGA, and PEG may be solely coated individually, or required materials among them may be also mixed to be coated. Also, such polymer materials may be separately coated, or when their physical properties are similar to those of medication, they may be mixed to be coated.

When the gel (g) is used for the purpose of anastomosing an artificial blood vessel, preferably, medication M capable of restraining the constriction of blood vessels and inflammation reaction may be used as a coating. For example, medication M such as paclitaxel, rapamycin, and the like, which can suppress excessive cell multiplication or an inflammation, may be used.

In case of coating the medication M using the gel (g) applied to the exemplary embodiment of the present invention, the medication can be formed to be more easily coated on the source thread T using a silk material, and it is also possible to be applicable to a source thread T using a material such as polypropylene.

Embodiment 1

Figure 5:
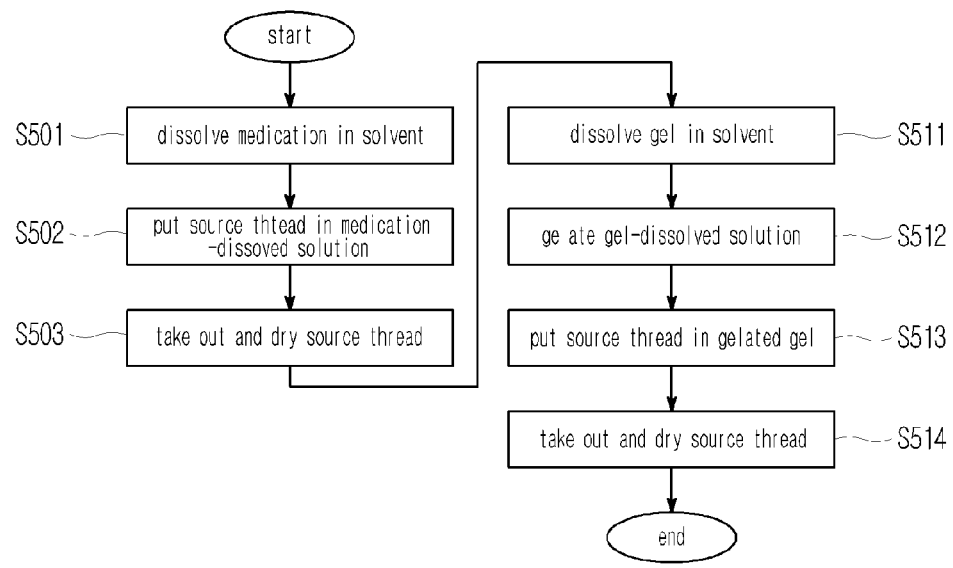
FIG. 5 is a flow chart that describes a method for coating medication according to the first exemplary embodiment of the present invention.

A method for coating medication on a medical article according to a first embodiment of the present invention will be described with reference to FIG. 5, and the suture 10 using the medication coating method illustrated in FIG. 5 will be described with reference to FIG. 2.

1. Dissolve Medication (S501)

The medication M to be coated on the surface of the source thread (T) is dissolved in a solvent (S501). The medication (M) used herein may correspond to a material or the like that can suppress the generation of an inflammation and quickly heal an injury without a scar or a material that can suppress the contraction of blood vessels, and a suitable medication (M) may be coated on the source thread (T).

2. Put Source Thread in a Solution (S502)

The source thread (T) is put in a solution in which the medication (M) has been dissolved (S502). In this step, the medication (M) is coated on the source thread (T) to form a medication coated layer.

Meanwhile, in coating the medication M, besides the method of coating the source thread T by putting it in the medication M-dissolved solution, the medication M may be jetted using a spray so as to coat the source thread T.

3. Dry Source Thread (S503)

The medication-coated source thread T is dried to complete the medication coating (S503). At this step, after the source thread (T) is coated with the medication (M), it is dried to allow the gel (g) to be coated on the surface of the source thread (T) which has been coated with the medication (M).

4. Dissolve Gel (S511)

The gel (g) is dissolved in a solution so as to coat the surface of the medication-coated source thread T (S511). Gelatin, dextran, and glyceraldehyde or glutaraldehyde are mixed to generate gel (g) in an aqueous state.

For example, a certain amount of gelatin is dissolved in water and incubated at 37° C., and then dextran and glyceraldehyde are mixed, dissolved in water and then sufficiently stirred. Afterwards, the two types of solutions are mixed and incubated at 37° C. for gelation.

5. Gelation (S512)

The gel (g) in an aqueous state is gelated with a time lapse, and in this case, the amount of gel (g) coated on the source thread T can be adjusted according to the gelation state (S512). Thus, by putting the source thread T according to a desired gelation state, the amount of gel (g) coated on the source thread T can be adjusted.

When the viscosity increases as the gelation is prolonged in the aqueous state, a large amount of gel (g) can be coated on the source thread T due to the viscosity, and at an initial stage where the gelation has just been started, a small amount of gel (g) can be coated due to the relatively low viscosity.

In addition, the speed at which the medication M spurts out may vary according to the state in which the gel (g) is gelated, and a time duration in which the gel (g) is coated on the source thread T and gelated may vary according to the density of the component of the gel (g) or the temperature.

6. Put Source Thread in the Gel (S513)

The source thread T is put in the gel (g) in the gelation state to coat the gel (g). The gel (g) is coated on the surface which has been coated with the medication M (S513).

In this case, the gel (g) coated on the surface of the source thread T has the characteristics of having a rough surface, so a step of coating a material for smoothing the surface of the gel (g)) on the surface of the gel (g) may be additionally performed.

In that case, the material for smoothing the surface of the gel (g) may include polycaprolactone (PCL), polyglycolic acid (PGA), polylactic acid (PLA), polylactic-co-glycolic acid (PLGA), polyethylene glycol (PEG), etc.

7. Dry Source Thread (S514)

Figure 2:
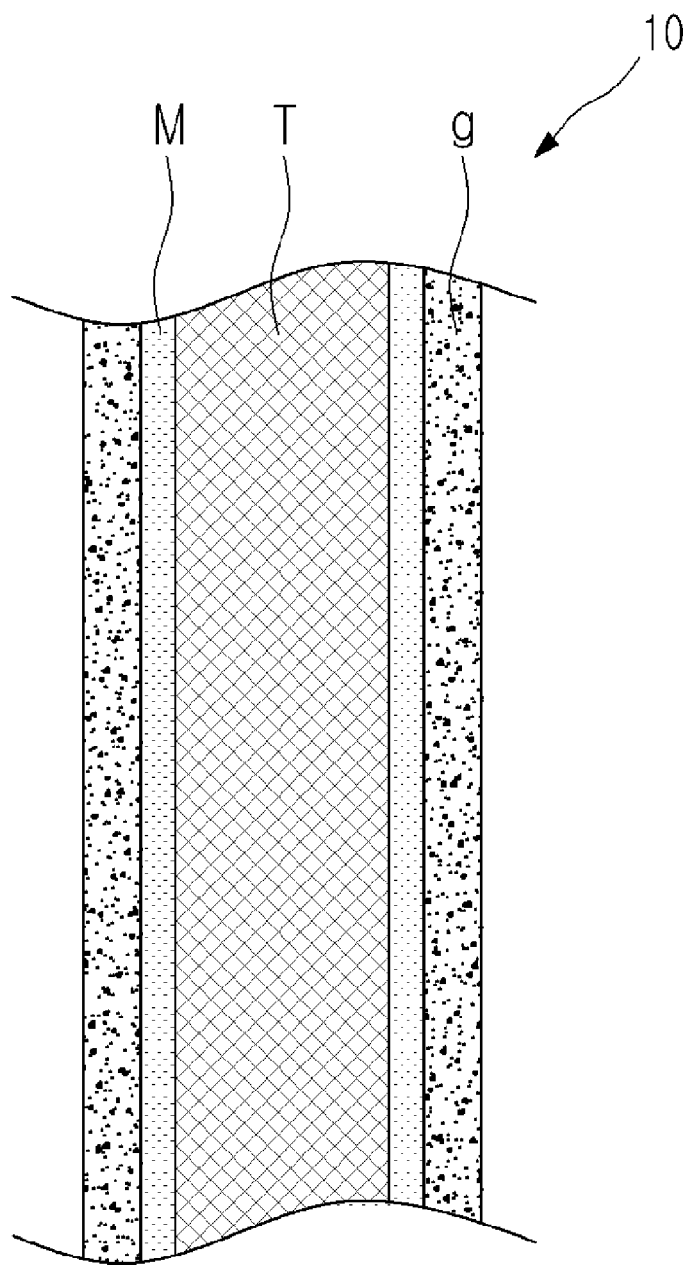
FIG. 2 illustrates a suture according to a first exemplary embodiment of the present invention.

The source thread T coated with the gel (g) is dried, completing the coating of the medication M and creating the suture 10 having such a form as shown in FIG. 2 (S514).

Meanwhile, the flow of steps S511 and S512 in the first embodiment may be changed for the convenience of the process.

Embodiment 2

Figure 6:
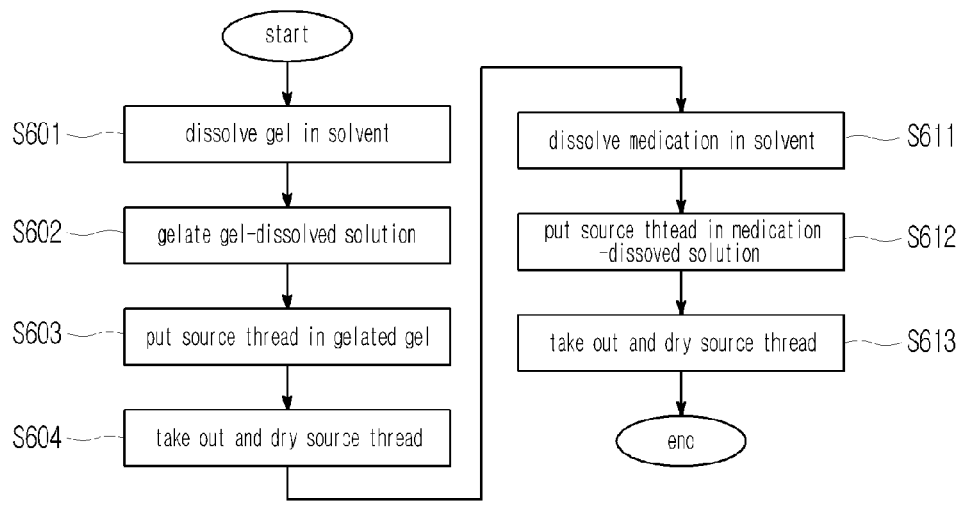
FIG. 6 is a flow chart that describes a method for coating medication according to the second exemplary embodiment of the present invention.

A method of coating medication on the suture 10 according to a second embodiment of the present invention will be described with reference to FIG. 6, and the suture 10 using the medication coating method illustrated in FIG. 6 will be described with reference to FIG. 3.

1. Dissolve gel (S601)

gel (g) is dissolved in a solvent so as to coat on the surface of the source thread (T) (S601). Here, the repeated description with respect to step S511 according to the first embodiment as described above will be omitted.

2. Gelation (S602)

The gel (g) in the aqueous state is gelated with the lapse of time (S602). This step may refer to step S512 in the first embodiment as described above.

3. Put Source Thread in the Gel (S603)

The source thread T is put in the gel (g) in a gelated state so as to be coated with the gel (g) (S603).

4. Dry Source Thread (S604)

The gel coated on the source thread T is dried (S604).

5. Dissolve Mediation (S611)

In order to coat the medication M on the gel-coated source thread T, the medication M is dissolved (S611). A description of this step will be omitted with reference to the first embodiment as described above.

6. Put Source Thread in Medication-Dissolved Solution (S612)

The gel-coated source thread T is put in the medication-dissolved solution (S612). The repeated description of this process will be omitted with reference to step S513 in the first embodiment.

Meanwhile, in coating the medication (M), besides the method of coating the source thread (T) by putting it in the medication (M)-dissolved solution, the medication (M) may be jetted using a spray to coat on the source thread (T).

7. Dry Source Thread (S613)

Figure 3:
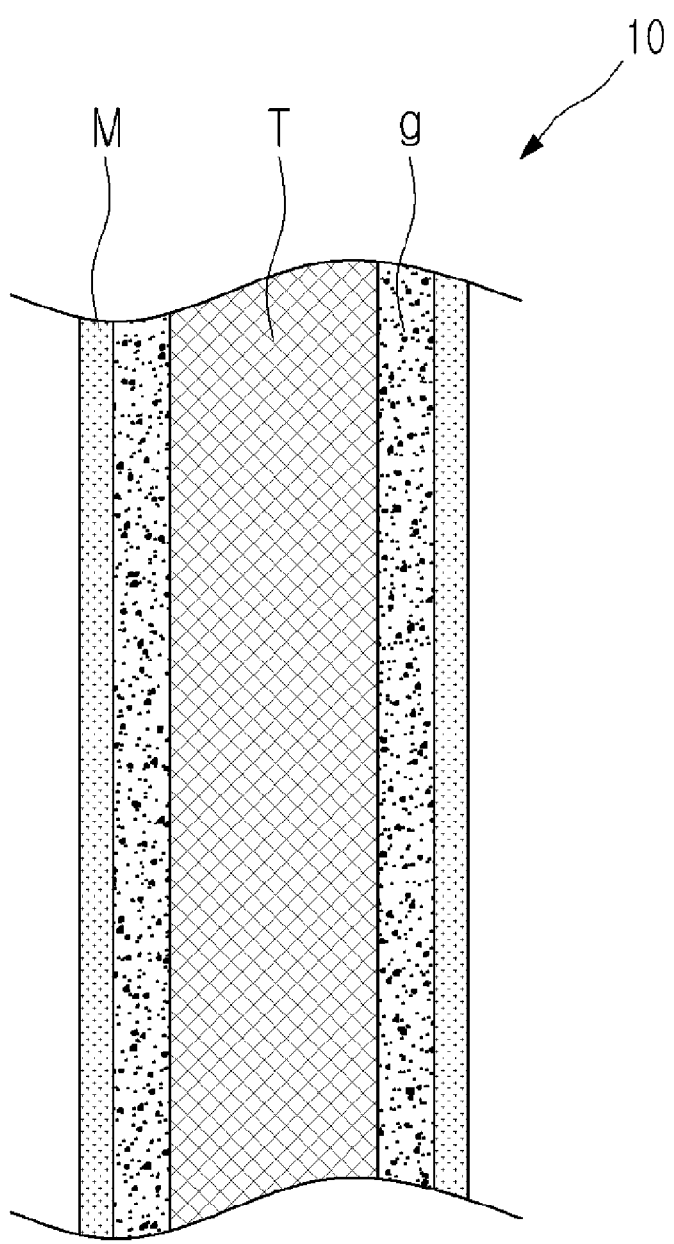
FIG. 3 illustrates a suture according to a second exemplary embodiment of the present invention.

The medication M coating-completed source thread T is dried to create the suture 10 as shown in FIG. 3 (S613).

Meanwhile, the flow of step S611 in the second embodiment may be changed for the convenience of the process.

Embodiment 3

Figure 7:
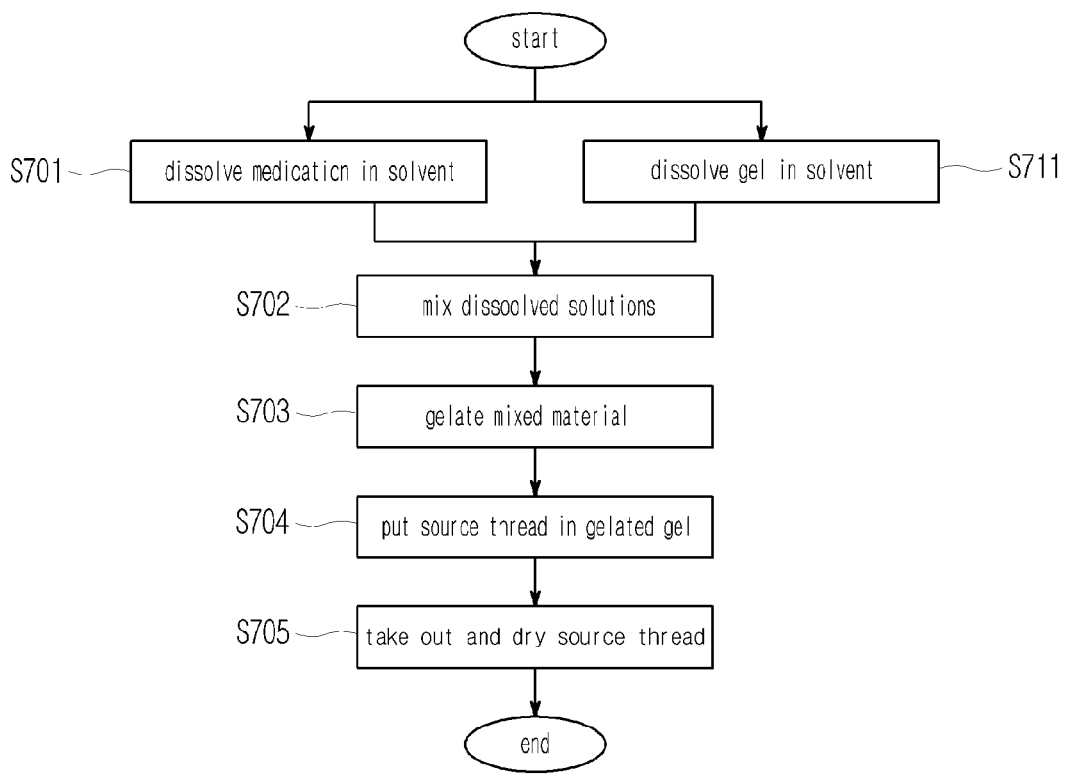
FIG. 7 is a flow chart that describes a method for coating medication according to the third exemplary embodiment of the present invention.

A method of coating medication on the suture 10 according to a third embodiment of the present invention will be described with reference to FIG. 7, and the suture 10 using the medication coating method illustrated in FIG. 7 will be described with reference to FIG. 4.

1. Dissolve Medication (S701)

The medication M to be coated on the surface of the source thread T is dissolved in a solvent (S701). The medication (M)

used herein may correspond to a material or the like that can suppress the generation of an inflammation and quickly heal an injury without a scar or a material that can suppress the contraction of blood vessels, and a suitable medication M may be coated on the source thread T.

Meanwhile, preferably, an aqueous medication is used so as to be mixed with gel (g) in an aqueous state to generate a mixture material G (S702) (to be described).

2. Dissolve Gel (S711)

The gel (g) to be coated on the surface of the source thread T is dissolved in a solution (S711). Gelatin, dextran, and glyceraldehyde or glutaraldehyde are mixed to generate gel (g) in an aqueous state.

3. Mix (S702)

The solution in which the medication M has been dissolved in step S701 and the gel (g) in the aqueous state in step S711 are mixed to create a mixture material G (S702). The source thread T may be coated with the mixture material G.

4. Gelation (S703)

The mixture material G is gelated with the lapse of time, and in this case, the amount of gel (g) coated on the source thread T can be adjusted according to the gelation state (S703).

5. Put Source Thread in the Gel (S704)

When the mixture material G is gelated with a proper viscosity (S704), the source thread T is put in so as to be coated with the mixture material G, and in this case, a proper amount of gel (g) can be coated according to the viscosity varying according to the gelation process.

Meanwhile, the surface of the source thread T coated with the mixture material G may be rough due to the gel (g), so preferably, a step of coating a material for smoothing the surface of the gel (g) may be additionally performed, or a material for smoothing the surface of the gel (g) may be added to the mixture material G.

6. Dry Source Thread (S705)

Figure 4:
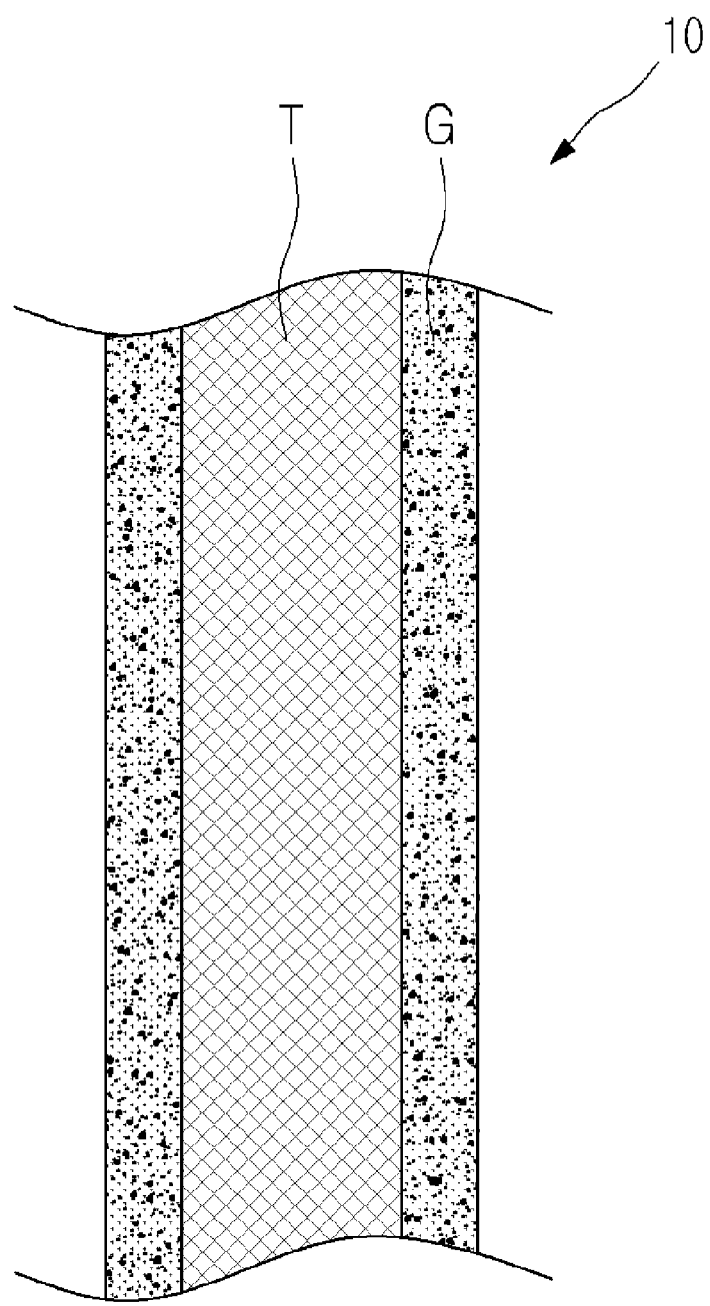
FIG. 4 illustrates a suture according to a third exemplary embodiment of the present invention.

The source thread T coated with the mixture material G is dried to complete the suture 10 having such as form as shown in FIG. 4 (S705).

As described above, in the present invention, coating medication on a medical product using gel, coating medication on an article made of silk and an article made of polypropylene as well as coating water-soluble medication can be facilitated.

In addition, after the medication is coated, in the case of a gel-coated article, an article coated with medication after being coated with gel, and an article coated with a material obtained by mixing gel and medication, the speed at which coated medication spurts out can be adjusted using viscosity that varies according to gelation of the gel.

Also, medication can be stably coated on an article owing to the gel, and a coated state of medication can last for a long time.

Meanwhile, a gel-coated article, an article coated with medication after being coated with gel, and an article coated with a material obtained by mixing gel and medication can be suitably used for patients according to circumstances.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A method for coating medication of a medical product, the method comprising:
    coating medication on the surface of an article used for a medical purpose; and
    coating gel in a viscous semisolid state on the surface of the medication-coated article, wherein the gel is a mixture of gelatin, dextran, and glyceraldehyde.

2. The method of claim 1, wherein the article is source thread.

3. The method of claim 1, wherein the gelatin, dextran, and glyceraldehyde are mixed in an aqueous solution state.

4. The method of claim 1, further comprising:
    a gel surface coating step of coating a material for smoothing the surface of the gel on the surface of the article after the article is coated with the gel.

5. The method of claim 4, wherein the material for smoothing the surface of the gel is one or more of polycaprolactone (PCL), polyglycolic acid (PGA), polylactic acid (PLA), poly-lactic-co-glycolic acid (PLGA), and polyethylene glycol (PEG).

6. The method of claim 1, wherein after the gel is coated on the surface of the article, a material for smoothing the surface of the gel is further coated.

7. The method of claim 6, wherein the material for smoothing the surface of the gel is one or more of polycaprolactone (PCL), polyglycolic acid (PGA), polylactic acid (PLA), poly-lactic-co-glycolic acid (PLGA), and polyethylene glycol (PEG).

8. The method of claim 1, wherein the amount of the gel coated on the article is adjustable according to gelation of the gel.

9. The method of claim 1, wherein a speed at which the medication spurts out varies according to a gelation state of the gel.

10. The method of claim 1, wherein time during which the gel is coated and gelated on the article varies according to density and temperature of the gel.

11. A method for coating medication of a medical product, the method comprising:
    coating medication on the surface of an article used for a medical purpose; and
coating gel in a viscous semisolid state on the surface of the medication-coated article, wherein the gel is a mixture of gelatin, dextran, and glutaraldehyde.

12. The method of claim 11, wherein the gelatin, dextran, and glutaraldehyde are mixed in an aqueous solution state.

* * * * *